(12) United States Patent
Segall et al.

(10) Patent No.: US 6,288,097 B1
(45) Date of Patent: *Sep. 11, 2001

(54) STABILIZED ISOTHIAZOLINONE FORMULATIONS

(75) Inventors: Jeane Segall; Leonard Marshall Shorr, both of Haifa (IL)

(73) Assignee: Bromine Compounds, Ltd., Beer-Sheva (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/073,969

(22) Filed: Jun. 8, 1993

Related U.S. Application Data

(63) Continuation of application No. 07/815,325, filed on Dec. 27, 1991, now abandoned.

(30) Foreign Application Priority Data

Dec. 28, 1990 (IL) .......................................... 96820

(51) Int. Cl.⁷ .................................................. A01N 43/80
(52) U.S. Cl. ............................................................. 514/372
(58) Field of Search ............................... 548/213; 514/372

(56) References Cited

U.S. PATENT DOCUMENTS 4,920,137 * 4/1990 Segall et al. .......................... 548/213

FOREIGN PATENT DOCUMENTS

| 0166611 | 1/1986 | (EP) . |
| 0194146 | 9/1986 | (EP) . |
| 0300483 | 1/1989 | (EP) . |

OTHER PUBLICATIONS

Hart et al., Organic Chemistry, A Short Course, Ninth Ed., Houghton Mifflin Company, Boston; pp. 227, 282 and 283, 1995.*

* cited by examiner

*Primary Examiner*—Jane C. Oswecki
(74) *Attorney, Agent, or Firm*—Anderson, Kill & Olick, P.C.

(57) ABSTRACT

A composition comprising A) an aqueous solution wherein the total content of 3-isothiazolinones is below 8 wt/%, and B) a stabilizing compound of the formula:

$$[R_xA\text{---}C_6H_2R^1R^2]_y\text{---}Z$$

wherein:

R, $R^1$ and $R^2$ each independently represents hydrogen, a straight-chained or branched or cyclic alkyl radical, aralkyl or aryl;

A is oxygen or nitrogen;

Z represents $AR_x$, $R^1$, $R^2$, alkoxy methylene, methylene or alkylidene;

provided that when A is oxygen, x is 0 or 1 and when A is nitrogen, x is 1 or 2; and y is 1 or 2;

exhibits improved stability.

35 Claims, No Drawings

STABILIZED ISOTHIAZOLINONE FORMULATIONS

This application is a continuation of application Ser. No. 07/815,325, filed Dec. 27, 1991 now abandoned.

BACKGROUND OF THE INVENTION

1. Field of the Invention

The present invention relates to improvements in the stabilization of isothiazolinones, more particularly the stabilization of 3-isothiazolinones of the formula (1):

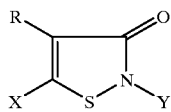

(1)

wherein X represents hydrogen or a halogen, Y is an alkyl, alkenyl, cycloalkyl, aralkyl or aryl group and R is hydrogen, halogen or an alkyl radical.

2. The Prior Art

Such compounds are known to possess biocidal and biostatic activity towards a variety of organisms. The isothiazolinones of this type, however, are often not obtained in free form, but as complexes of the formula (2):

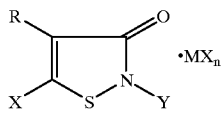

(2)

wherein M is a metallic or an amino cation, X is an anion forming a compound with the cation M, and the value of n is such that the anion Xn satisfies the valence of M. The complexes of formula (2), described in U.S. Pat. No. 4,067,878, are said to be more stable than the 3-isothiazolones of formula (1).

The term alkyl group for the substituents R and Y is intended to include both unsubstituted or substituted alkyl, alkenyl, cycloalkyl, aralkyl or aryl groups. In a preferred embodiment the alkyl group is selected from methyl and n-octyl.

Examples of the cation M are metal cations such as calcium, copper, magnesium, manganese, nickel, sodium, potassium and zinc and complexes of the metal ions such as complexes with ammonia and amines.

For bactericidal and fungicidal purposes, particularly useful compositions, described in U.S. Pat. No. 4,105,431, comprise a mixture of N-alkyl-isothiazolin-3-one and N-alkyl-5-chloro-isothiazolin-3-one, in a weight ratio of about 1:3 respectively. A particularly useful mixture of this kind is that in which Y is a methyl group, and such a mixture is referred to hereinafter as MIT (methylisothiazolinones).

Formulations of MIT in water or in solvent media containing hydroxylic groups are unstable, decompose rapidly and cannot be stored for long periods of time. The art has searched for ways to overcome this stability problem for a long time. A solution suggested in the art comprises stabilizing 3-isothiazolinones either in liquid formulations or on solid supports, by the addition of metal nitrates. Some such methods are described, e.g., in U.S. Pat. Nos. 3,870,795, 4,067,878, EP 0 106 563 and EP 0 166 611. Such methods have the considerable drawback of requiring the addition of metal nitrates in amounts which are usually nearly equimolar—but often even in excess—with respect to the 3-isothiazolinones. MIT, being a very effective biocide, is often required in application in very low concentrations of the active ingredient (a.i.). For such purposes, it is more convenient to provide MIT formulations of low a.i. concentrations. However, commercially available formulations stabilized only by large concentrations of nitrate salts become less stable on dilution. Furthermore, the addition of nitrates may lead to the presence of nitrosamines, which are highly undesirable impurities which are suspected of being carcinogens. Therefore, some of the methods of the art have the added disadvantage of requiring means for removing such nitrosamines or their precursors, as disclosed, e.g., in EP 0 095 907, or for inhibiting their formation. Such operations are complicated, time-consuming and do not afford the certainty that a sufficient amount of nitrosamines or of their precursors has been removed.

Another disadvantage in the use of metal nitrate stabilization is that in the application of such formulae for the protection of latex-based products (e.g., in paints), these salts may cause undesirable coagulation. This is particularly true in the case when di- and polyvalent metallic ions are present in the MIT formulation.

An effective method for stabilizing MIT is described in U.S. Pat. No. 4,920,137 of the same inventors, which is characterized in that a stabilizing effective amount of a stabilizing compound of the formula (3):

(3)

wherein:

R, $R^1$ and $R^2$ each independently represents hydrogen, a straight-chained or branched or cyclic alkyl radical, aralkyl or aryl;

A is oxygen or nitrogen;

Z represents $AR_x$, $R^1$, $R^2$, alkoxy methylene, methylene or alkylidene; provided that when A is oxygen, x is 0 or 1 and when A is nitrogen, x is 1 or 2; and y is 1 or 2;

is added to the composition containing a 3-isothiazolinone or two or more 3-isothiazolinones.

A preferred group of stabilizers, which possess enhanced stabilization properties, consists essentially of hydroquinone, quinone and quinhydrone, and their derivatives and homologues. Other representative stabilizing compounds are, e.g., tert-butylcatechol, p-methoxyphenol, and p-phenylenediamine and its derivatives.

According to a preferred embodiment of the said invention, the composition to be stabilized comprises a mixture of N-alkyl-isothiazolin-3-one and N-alkyl-5-chloro-isothiazolin-3-one. Particularly useful mixtures of this kind are those in which the N-alkyl radical is a N-methyl radical.

The said patent is also directed to stable compositions containing one or more 3-isothiazolinones and a stabilizing effective amount of a compound of the formula (3):

(3)

wherein:

R, $R^1$, $R^2$, A, Z, x and y have the meanings described above.

While the presence of metal nitrate stabilizers in the compositions is not necessary, such nitrate stabilizers could be also added, together with the said stabilizing compound (s). Adding to the composition to be stabilized also one or more metal salt(s), selected from metal nitrate stabilizers and salts of metals of groups IA and IIA of the periodic table of the elements, provides a synergistic stabilizing effect, and may be convenient in some cases. In any case, the synergistically effective amount of metal nitrate stabilizers employed in any given composition of U.S. Pat. No. 4,920,137 can be much lower than amounts used in the known art, and hence the amount of nitrosamines or nitrosamine precursors would be drastically reduced.

By "synergistically effective amounts" is meant any amount which, while by itself incapable of effectively stabilizing 3-isothiazolinones, improves the stabilization of 3-isothiazolinone formulations which is provided by the sole addition of stabilizing effective amounts of stabilizing compounds of formula (3).

Preferred metal salts are selected from the group consisting of magnesium nitrate, $K_2HPO_4$, KH phthalate, magnesium acetate, $NaNO_3$, $KNO_3$ and potassium permanganate.

Preferred stabilizing compounds comprise hydroquinone, quinone and quinhydrone, and their derivatives and homologues.

SUMMARY OF THE INVENTION

It is an object of the present invention to provide improvements in the method and compositions of U.S. Pat. No. 4,920,137, which result in compositions which are stable for long periods, require smaller amounts of stabilizers and, in general, exhibit improved stability characteristics.

The inventors have surprisingly found, and this is an object of the present invention, that it is possible to provide improved shelf life of 3-isothiazolinone aqueous compositions simply by storing them in form, e.g., 8 wt % total isothiazolinones or below. This is surprising, because normal aqueous compositions, e.g., commercial MIT-compositions stabilized only by metal nitrates become less stable on dilution. Thus, preparing a diluted solution of prior art formulations, e.g., below 8 wt %, requires the addition of more stabilizers.

It has further been surprisingly found, and this is another object of the invention, that improved results can be obtained by adding hydroquinone to MIT solutions conventionally stabilized with nitrate salts only.

Another object of the present invention is the use of monovalent cations in the synergy such as $NaNO_3$, and in only very low concentrations, by which means latex destabilization is obviated.

It has further been surprisingly found, and this is still another object of the present invention, that it is more effective to generate at least part of the hydroquinone in situ, by heating compositions comprising benzoquinone, which reacts to give hydroquinone, than by adding hydroquinone to the formulation as such. The skilled chemist will be able to devise an appropriate temperature/time path to effect the aging of the formulation containing benzoquinone, keeping in mind that the temperature/time path should not be excessive so as substantially to accelerate the decomposition of the isothiazolinones. Temperatures of about 40–90° C. can be conveniently employed for this purpose.

Furthermore, aging under aeration conditions, as described in U.S. Pat. No. 4,920,137 (col. 2, lines 30–45), has also been found to be effective with the diluted solutions described in this application.

In another aspect of the invention the isothiazolinones aqueous solution is pre-treated, prior to the addition of at least the major amounts of stabilizers by contacting it with active carbon. This contact can be effected in any suitable way, e.g., by stirring active carbon powder in the solution, followed by filtering. This procedure substantially improves the stability of the final composition. Surprisingly, active carbon treatment does not improve the stability of the prior art metal nitrate-stabilized isothiazolinone formulations.

As will be appreciated by the skilled chemist, all the above improvements work toward the preparation of an improved, more stable final composition, and their benefits can be combined as appropriate.

DETAILED DESCRIPTION OF THE PREFERRED EMBODIMENTS

The above and other characteristics and advantages of the invention will be better understood through the following illustrative and non-limitative examples thereof. The following examples represent stability tests performed at elevated temperatures, in order to accelerate decomposition. For reference purposes it should be noted that a correlation of the elevated temperature testing to ambient temperature is described in EP 0 166 611. For instance, for a formulation containing 1.5% of isothiazolinones one week at 50° C. was found to be equivalent to two months of storage at ambient temperature. The results obtained by the inventors confirm the above correlation. All percentages given in the following examples refer to weight percent.

The following examples refer to MIT as the representative formulation. MIT concentrations were determined in all cases by HPLC analysis. In the synthesis of MIT, mercaptoamides are cyclochlorinated in the presence of inert liquid media. The major part of the MIT produced generally precipitates. The product can be recovered in several ways, viz., by filtering off the precipitate and recycling the mother liquor, by evaporating the solvent leaving all the products in the residual solid, or by extracting the product into a second liquid phase, such as water, essentially insoluble in the reaction medium. While the method of the invention is valid for stabilizing MIT independent of its source, differences can be found between different samples, depending on their source. Care should therefore be exercised in comparing results, and results obtained in different examples employing different materials may not be comparable.

EXAMPLE 1

An aqueous MIT formulation made up to contain 14.6% Active Ingredients (A.I.), was stabilized by 2% hydroquinone (HQ) and 0.1% $NaNO_3$. Parts of this formulation were diluted with water to contain respectively 6.7%, 3.3% and 1.6% A.I. These four formulations were exposed to accelerated stability tests at 50° C. A composition was considered as destabilized when more than 10% MIT decomposition occurred. This limiting value is defined as the "Stability Period". The results obtained are summarized in Table I:

TABLE I

| MIT Concentration | Stability Period at 50° |
|---|---|
| 13% | ~100 days |
| 7% | ~180 days |
| 3.5% | ~8 months |
| 1.6% | Stable after 8 months |

EXAMPLE 2

Example 1 was repeated, using as stabilizers in the original formulation 1% HQ and 0.1% $NaNO_3$. The results are summarized in Table II:

TABLE II

| MIT Concentration | Stability Period at 50° C. |
|---|---|
| 14% | ~70 days |
| 7% | ~110 days |
| 4% | Stable after 7 months |

EXAMPLE 3

To an aqueous solution made up to contain 13% A.I. and ~11% Mg nitrate, there was added 1% HQ. This formulation was diluted to 6.5% and 3% A.I. respectively, and the accelerated stability test performed at 50° C. The results obtained are summarized in Table III:

TABLE III

| MIT Concentration | Stability Period at 50° C. |
|---|---|
| 13% | ~75 days |
| 6.5% | ~100 days |
| 3% | ~100 days |

EXAMPLE 4

Example 3 was repeated, the difference being that 2% HQ was added to the aqueous solution, instead of 1% HQ. The results are summarized in Table IV:

TABLE IV

| MIT Concentration | Stability Period at 50° C. |
|---|---|
| 7% | 5 months |
| 3.5% | Stable after 8 months |

EXAMPLE 5

When Example 3 was repeated without the addition of HQ, the "Stability Periods" decreased to 35 to 25 days, at MIT concentration levels of 14% to 3.5% respectively.

EXAMPLE 6

An aqueous MIT solution was made up to contain ~15% A.I. One hundred gr. was mixed with 6 gr. of active carbon (Merck grade) and stirred at ambient temperature for 10 minutes. After filtration, the MIT solution was stabilized by 1% HQ. This formulation was diluted with water to 7.5% and 3.6% A.I. respectively. The results of the accelerated stability tests are summarized in Table V:

TABLE V

| MIT Concentration | Stability Period at 50° C. |
|---|---|
| 15% | ~68 days |
| 7.5% | ~130 days |
| 3.6% | ~180 days |

EXAMPLE 7

Example 6 was repeated without treating the 15% a.i. formulation with active carbon. The "Stability Period" was reduced to ~4 days.

EXAMPLE 8

Samples of commercially available MIT formulations (Kathon 886, Rohm & Haas) were tested. One sample was treated with active carbon (Merck, ex. pure Grade), 6 gr/100 gr formulation, by mixing it at ambient temperature during 10 minutes followed by filtration. The filtrate and the untreated Kathon formulation were compared in accelerated stability tests, performed at 90° C. The results obtained do not show any improvement in stability for the active carbon-treated sample.

EXAMPLE 9

An aqueous MIT formulation made up to contain 13% A.I. (Active Ingredients) was neutralized and treated with active carbon (Merck, ex. pure), 6 gr. carbon/100 gr. formulation. The mixture was stirred magnetically during 10 minutes at ambient temperature and filtered. Hydroquinone (HQ), 1% was added to the filtrate and the stability of the formulation was measured by the "Accelerated Test" at 50° C. In parallel, the stability of part of the formulation which was not treated with active carbon, but was stabilized by 1% HQ was exposed to the same stability test. The following results were obtained (Table VI):

TABLE VI

| Sample No. | Treatment | Stability Period at 50° C. |
|---|---|---|
| 1 | None | 4 days |
| 2 | Active Carbon | 58 days |

EXAMPLE 10

An aqueous MIT formulation was made up to contain ~14% A.I. and 0.7% benzoquinone (BQ)+0.1% $NaNO_3$. The formulation was heated 40 hours at 50° C., whereby the concentration of BQ was reduced by half and HQ formed instead. An additional 0.5% of HQ was added and the stability of the resultant formulation examined at 40° C. The Stability Period at this temperature was found to be 60 days. When the same formulation was stabilized with 1% HQ+0.1% $NaNO_3$, the Stability Period at 40° C. was found to be 10 days.

EXAMPLE 11

50 parts by weight of an aqueous MIT formulation containing 13.5% A.I., 2% HQ and 0.1% $NaNO_3$ was mixed at ambient temperature with 50 parts by weight of Emulsin (a PVA-based aqueous emulsion paint, Tambour, Israel). A uniform composition was obtained.

This procedure was repeated, but replacing the aqueous MIT formulation with Kathon 886. A heterogeneous composition was obtained upon mixing.

EXAMPLE 12

Ap aqueous MIT formulation made up to contain 12.5 A.I. was divided in two parts: to one half there was added HQ+$NaNO_3$ and to the other half there was added HQ+KNO3. Both were exposed to the "accelerated stability test" at 50° C. The results obtained are summarized in Table VII below, expressed as "Stability Period at 50° C." (S.P.-50).

TABLE VII

| Stabilizer | S.P.-50 |
|---|---|
| 1% HQ + 1% NaNO$_3$ | 60 days |
| 1% HQ + 1% KNO$_3$ | 60 days |
| 1% HQ + 5% NaNO$_3$ | 60 days |
| 1% HQ + 5% KNO$_3$ | 60 days |

What we claim is:

1. A stabilized composition comprising an aqueous solution of one or more 3-isothiazolinones of the Formula (1)

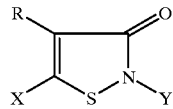
(1)

wherein X represents hydrogen or a halogen, Y is an alkyl, alkenyl, cycloalkyl, aralkyl or aryl group and R is hydrogen, halogen or an akyl radical, and a stabilizing amount of a compound of the formula:

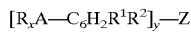
[R$_x$A—C$_6$H$_2$R$^1$R$^2$]$_y$—Z wherein:
R,R$^1$ and R$^2$ each independently represents hydrogen, a straight-chained or branched or cyclic acid alkyl radical, aralkyl or aryl;
A is oxygen or nitrogen;
C$_6$H$_2$ is a phenyl ring which may be substituted;
Z represents Ar$_x$, R$^1$,R$^2$, alkoxy methylene or alkylidene;
provided that when A is oxygen, x is 0 or 1 and when A is nitrogen, x is 1 or 2; and y is 1 or 2;
wherein the total content of 3-isothiazolinones is below 8 wt % and which contains no more than 10 wt. % isothiazolinone decomposition products.

2. A stabilized composition comprising an aqueous solution of one or more 3-isothiazolinones of the Formula (1)

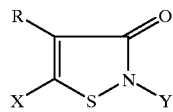
(1)

wherein X represents hydrogen or a halogen, Y is an alkyl, alkenyl, cycloalkyl, aralkyl or aryl group and R is hydrogen, halogen or an alkyl radical,
and a stabilizing amount of a compound of the formula:

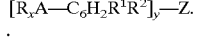
[R$_x$A—C$_6$H$_2$R$^1$R$^2$]$_y$—Z.

wherein:
R,R$^1$ and R$^2$ each independently represents hydrogen, a straight-chained or branched or cyclic alkyl radical, aralkyl or aryl;
A is oxygen or nitrogen;
C$_6$H$_2$ is a phenyl ring which may be substituted;
Z represents Ar$_x$,R$^1$, R$^2$, alkoxy methylene or alkylidene;
provided that when A is oxygen, x is 0 or 1 and A is nitrogen, x is 1 or 2; and y is 1 or2;
wherein the total content of 3-isothiazolinones is below 8 wt. % and wherein the composition has a stability period of at least 100 days.

3. A stabilized composition comprising an aqueous solution of one or more 3-isothiazolinones of the Formula (1)

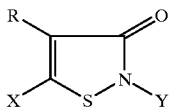
(1)

wherein X represents hydrogen or a halogen, Y is an alkyl, alkenyl, cycloalkyl, aralkyl or aryl group and R is hydrogen, halogen or an akyl radical,
and a stabilizing amount of a compound of the formula:

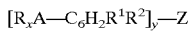
[R$_x$A—C$_6$H$_2$R$^1$R$^2$]$_y$—Z wherein:
R, R$^1$ and R$^2$ each independently represents hydrogen, a straight-chained or branched or cyclic alkyl radical, aralkyl or aryl;
A is oxygen or nitrogen;
C$_6$H$_2$ is a phenyl ring which may be substituted;
Z represents Ar$_x$,R$^1$,R$^2$, alkoxy methylene or alkylidene;
provided that when A is oxygen, x is 0 or 1 and when A is nitrogen, x is 1 or 2; and y is 1 or 2;
wherein the total content of 3-isothiazolinones is below 8 wt. % and which contains no more than 10 wt. % isothiazolinone decomposition products and wherein the composition has a stability period of at least 100 days.

4. A composition according to claim 1, wherein the stabilizing compound is selected from the group consisting of tert-butylcatechol, p-methoxyphenol, p-phenylenediamine, N,N'-di-sec-butyl-p-phenylenediamine, N,N'-diisopropyl-p-phenylenediamine, tert-butyl-hydroxyanisole, hydroquinone, quinhydrone, and their mixtures and derivatives.

5. A composition according to claim 1, further comprising a metal nitrate synergist.

6. A composition according to claim 5, wherein the metal nitrate synergist is monovalent metal nitrate.

7. A composition according to claim 5, wherein the stabilizing compound is selected from the group consisting of hydroquinone and quinhydrone.

8. A composition according to claim 5, wherein the stabilizing compound is selected from the group consisting of hydroquinone and quinhydrone, together with a synergistic amount of a compound selected from the group consisting of NaNO$_3$, KNO$_3$. and a mixture of NaNO$_3$ and KNO$_3$.

9. A composition according to claim 1, wherein said one or more 3-isothiazolinones comprises N-methyl-isothiazolin-3-one and N-methyl-5-chloro-isothiazolin-3-one.

10. A composition according to claim 4, further comprising a metal nitrate synergist.

11. A composition according to claim 10, wherein the stabilizing compound is selected from the group consisting of hydroquinone and quinhydrone.

12. A composition according to claim 11, wherein the stabilizing compound is selected from the group consisting of hydroquinone and quinhydrone together with a synergistic amount of a compound and selected from the group consisting of NaNO$_3$, KNO$_3$ and a mixture of NaNO$_3$ and KNO$_3$.

13. A composition according to claim 2, wherein the stabilizing compound is selected from the group consisting of tert-butylcatechol, p-methoxyphenol, p-phenylenediamine, N,N'-di-sec-butyl-p-phenylenediamine, N,N'-diisopropyl-p-phenylenediamine, tert-butyl-hydroxyanisole, hydroquinone, quinhydrone, and their mixtures and derivatives.

14. A composition according to claim 2, further comprising a metal nitrate synergist.

15. A composition according to claim 14, wherein the metal nitrate synergist is monovalent metal nitrate.

16. A composition according to claim 14, wherein the stabilizing compound is selected from the group consisting of hydroquinone and quinhydrone.

17. A composition according to claim 14, wherein the stabilizing compound is selected from the group consisting of hydroquinone and quinhydrone, together with a synergistic amount of a compound selected from the group consisting of $NaNO_3$, $KNO_3$. and a mixture of $NaNO_3$ and $KNO_3$.

18. A composition according to claim 2, wherein said one or more 3-isothiazolinones comprises N-methyl-isothiazolin-3-one and N-methyl-5-chloro-isothiazolin-3-one.

19. A composition according to claim 13, further comprising a metal nitrate synergist.

20. A composition according to claim 19, wherein the stabilizing compound is selected from the group consisting of hydroquinone and quinhydrone.

21. A composition according to claim 20, wherein the stabilizing compound is selected from the group consisting of hydroquinone and quinhydrone together with a synergistic amount of a compound and selected from the group consisting of $NaNO_3$, $KNO_3$ and a mixture of $NaNO_3$ and $KNO_3$.

22. A composition according to claim 3, wherein the stabilizing compound is selected from the group consisting of tert-butylcatechol, p-methoxyphenol, p-phenylenediamine, N,N'-di-sec-butyl-p-phenylenediamine, N,N'-diisopropyl-p-phenylenediamine, tert-butyl-hydroxyanisole, hydroquinone, quinhydrone, and their mixtures and derivatives.

23. A composition according to claim 3, further comprising a metal nitrate synergist.

24. A composition according to claim 23, wherein the metal nitrate synergist is monovalent metal nitrate.

25. A composition according to claim 23, wherein the stabilizing compound is selected from the group consisting of hydroquinone and quinhydrone.

26. A composition according to claim 23, wherein the stabilizing compound is selected from the group consisting of hydroquinone and quinhydrone, together with a synergistic amount of a compound selected from the group consisting of $NaNO_3$, $KNO_3$. and a mixture of $NaNO_3$ and $KNO_3$.

27. A composition according to claim 3, wherein said one or more 3-isothiazolinones comprises N-methyl-isothiazolin-3-one and N-methyl-5-chloro-isothiazolin-3-one.

28. A composition according to claim 22, further comprising a metal nitrate synergist.

29. A composition according to claim 28, wherein the stabilizing compound is selected from the group consisting of hydroquinone and quinhydrone.

30. A composition according to claim 29, wherein the stabilizing compound is selected from the group consisting of hydroquinone and quinhydrone together with a synergistic amount of a compound and selected from the group consisting of $NaNO_3$, $KNO_3$ and a mixture of $NaNO_3$ and $KNO_3$.

31. A composition according to claim 4, wherein hydroquinone is generated in situ from benzoquinone.

32. A composition according to claim 6, wherein hydroquinone is generated in situ from benzoquinone.

33. A composition according to claim 7, wherein hydroquinone is generated in situ from benzoquinone.

34. A composition according to claim 11, wherein hydroquinone is generated in situ from benzoquinone.

35. A composition according to claim 12, wherein hydroquinone is generated in situ from benzoquinone.

* * * * *